(12) United States Patent
Bennett (10) Patent No.: US 11,206,977 B2
(45) Date of Patent: Dec. 28, 2021

(54) VISION TEST FOR DETERMINING RETINAL DISEASE PROGRESSION

(71) Applicant: The Trustees of the University of Pennsylvania, Philadelphia, PA (US)

(72) Inventor: Jean Bennett, Bryn Mawr, PA (US)

(73) Assignee: The Trustees of the University of Pennyslvania, Philadelphia, PA (US)

( * ) Notice: Subject to any disclaimer, the term of this patent is extended or adjusted under 35 U.S.C. 154(b) by 82 days.

(21) Appl. No.: 15/524,126

(22) PCT Filed: Nov. 4, 2015

(86) PCT No.: PCT/US2015/058958
§ 371 (c)(1),
(2) Date: May 3, 2017

(87) PCT Pub. No.: WO2016/073556
PCT Pub. Date: May 12, 2016

(65) Prior Publication Data
US 2017/0354324 A1    Dec. 14, 2017

Related U.S. Application Data

(60) Provisional application No. 62/077,286, filed on Nov. 9, 2014.

(51) Int. Cl.
*A61B 3/032*    (2006.01)
*A61B 3/06*    (2006.01)
*A61B 3/00*    (2006.01)

(52) U.S. Cl.
CPC ............ *A61B 3/032* (2013.01); *A61B 3/0041* (2013.01); *A61B 3/06* (2013.01); *A61B 3/063* (2013.01)

(58) Field of Classification Search
CPC ......... A61B 3/028; A61B 3/024; A61B 3/032; A61B 3/063; A61B 3/0041; A61B 3/0091;
(Continued)

(56) References Cited

U.S. PATENT DOCUMENTS 4,545,658 A    10/1985  Weiss
6,876,758 B1    4/2005  Polat et al.
(Continued)

OTHER PUBLICATIONS

Radner, W. et al., Reading performance of monofocal pseudophakic patients with and without glasses under normal and dim light conditions, Journal of Cataract and Refractive Surgery, Mar. 2014, 40(3):369-375.
(Continued)

*Primary Examiner* — Mustak Choudhury
(74) *Attorney, Agent, or Firm* — Colleen M. Schaller; Howson & Howson LLP (57) ABSTRACT

The present invention provides a reading test to measure vision loss. In one embodiment, the vision loss is due to disease progression. The tests are useful in evaluating the effects of intervention in vision deterioration. The tests are non-invasive, simple, quick, sensitive, reproducible, and easy to administer. The tests measure the subject's reading speed and accuracy under defined conditions of illumination and contrast. The results of these tests may be used to determine if treatment of a disease should be initiated, terminated, altered, or remain unchanged.

18 Claims, 1 Drawing Sheet

(58) Field of Classification Search
CPC .... A61B 3/06; A61B 5/16; A61H 5/00; G06F 19/00; G06F 19/3481; G16H 50/20; G16H 50/30; G16H 50/50; G16H 50/70; G16H 50/80; G16H 40/63; G09B 19/0023
See application file for complete search history.

(56) References Cited

U.S. PATENT DOCUMENTS

| | | | |
|---|---|---|---|
| 7,237,205 | B2 | 6/2007 | Sarel |
| 8,408,707 | B1 | 4/2013 | Watson et al. |
| 2002/0114783 | A1 | 8/2002 | Appukuttan et al. |
| 2004/0087843 | A1 | 5/2004 | Rice et al. |
| 2006/0078858 | A1* | 4/2006 | Vroman .................. A61B 5/16 434/179 |
| 2006/0216821 | A1 | 9/2006 | Totey et al. |
| 2007/0146631 | A1 | 6/2007 | Sinclair et al. |
| 2008/0278682 | A1 | 11/2008 | Huxlin et al. |
| 2010/0128223 | A1 | 5/2010 | Blumenthal et al. |
| 2013/0100402 | A1 | 4/2013 | Ooi et al. |
| 2013/0194317 | A1* | 8/2013 | Guillon .................. A61B 3/032 345/690 |
| 2014/0249491 | A1 | 9/2014 | Ballou, Jr. et al. |
| 2014/0285769 | A1 | 9/2014 | Palanker et al. |
| 2014/0320820 | A1 | 10/2014 | Kumarasamy et al. |
| 2015/0062535 | A1* | 3/2015 | Hawke .................... A61B 3/04 351/222 |
| 2015/0116667 | A1* | 4/2015 | High .................... A61B 3/0008 351/243 |

OTHER PUBLICATIONS

Barot, N. et al., Reading performance in infantile nystagmus, Ophthalmology, Jun. 2013, 120(6):1232-1238.

Dexl, A. K. et al., Reading performance and patient satisfaction after corneal inlay implantation for presbyopia correction: two-year follow-up, Journal of Cataract and Refractive Surgery, Oct. 2012, 38(10):1808-1816.

Rasp, M. et al., Bilateral reading performance of 4 multifocal intraocular lens models and a monofocal intraocular lens under bright lighting conditions, Journal of Cataract and Refractive Surgery, Nov. 2012, 38(11):1950-1961.

Dexl, A. K. et al., Reading performance after implantation of a modified corneal inlay design for the surgical correction of presbyopia: 1-year follow-up, American Journal of Ophthalmology, May 2012, 153(5):994-1001.

Burggraaff, M. C. et al., Feasibility of the Radner Reading Charts in low-vision patients, Graefe's Archive for Clinical and Experimental Ophthalmology, Nov. 2010, 248(11):1631-1637.

Gall, C. et al., Parafoveal vision impairments and their influence on reading performance and self-evaluated reading abilities, Graefe's Archive for Clinical and Experimental Ophthalmology, Jun. 2010, 248(6):863-875.

Finger, R. P. et al., Reading performance is reduced by parafoveal scotomas in patients with macular telangiectasia type 2, Investigative Ophthalmology & Visual Science, Mar. 2009, 50(3):1366-1370.

Maaijwee, K. et al., Reliability testing of the Dutch version of the Radner Reading Charts, Optometry and Vision Science, May 2008, 85(5):353-358.

Alió, J. L., et al., Design of short Spanish sentences for measuring reading performance: Radner-Vissum test, Journal of Cataract and Refractive Surgery, Apr. 2008, 34(4):638-642.

Kiss, C. G. et al., Reading performance of patients with uveitis-associated cystoid macular edema, American Journal of Ophthalmology, Oct. 2006, 142(4):620-624.

Stifter, E. et al., Monocular and binocular reading performance in children with microstrabismic amblyopia, British Journal of Ophthalmology, Oct. 2005, 89(10):1324-9.

Richter-Mueksch, Differences in reading performance of patients with Drusen maculopathy and subretinal fibrosis after CNV, Graefe's Archive for Clinical and Experimental Ophthalmology, Feb. 2006, 244(2):154-162.

Stifter, E. et al., Evaluating reading acuity and speed in children with microstrabismic amblyopia using a standardized reading chart system, Graefe's Archive for Clinical and Experimental Ophthalmology, Dec. 2005, 243(12):1228-1235.

Stifter, E. et al., Reading performance depending on the type of cataract and its predictability on the visual outcome, Journal of Cataract and Refractive Surgery, Jun. 2004, 30(6):1259-1267.

Stifter, E., Reliability of a standardized reading chart system: variance component analysis, test-retest and inter-chart relizbility, Graefe's Archvie for Clinical and Experimental Ophthalmology, Jan. 2004, 242(1):31-39.

Binkhorst, C. D. et al., Determination of the power of a convex-piano intraocular lens in situ from the dioptric keratometer reading of its front surface: extension table for the Javal-Schiotz ophthalmometer, British Journal of Ophthalmology, Jun. 1987, 1(6):473-476.

Colenbrander, A. et al., Low vision rehabilitation: visual acuity measurement in the low vision range, Journal of Ophthalmic Nursing Technology, Mar. 1992, 11(2):62-69.

International Search Report dated Jan. 13, 2016 in corresponding International Patent Application No. PCT/US15/58958, filed Nov. 4, 2015.

Written Opinion dated Jan. 13, 2016 in corresponding International Patent Application No. PCT/US15/58958, filed Nov. 4, 2015.

\* cited by examiner

Figure 1

VISION TEST FOR DETERMINING RETINAL DISEASE PROGRESSION

CROSS-REFERENCE TO RELATED APPLICATIONS

This application is a national stage of International Patent Application No. PCT/US2015/058958, filed Nov. 4, 2015, which claims the benefit of the priority of U.S. Provisional Patent Application No. 62/077,286, filed Nov. 9, 2014, which applications are incorporated herein by reference.

BACKGROUND

Gene therapy using adeno-associated virus (AAV) delivered to the retina is an effective strategy for amelioration or even of reversal of retinal and visual dysfunction. A challenge in demonstrating efficacy of retinal gene therapy for severe retinal degenerative disease, however, has been a lack of relevant outcome measures. Only one outcome measure has been defined as a "clinically meaningful" outcome measure—visual acuity (reading the eye chart). Visual acuity determines the efficacy of experimental treatments for a variety of retinal disorders. However, in many blinding conditions, visual acuity is irrelevant, either because it is preserved until very late in the disease, or that it is so poor, that the person is unable to read any letters at all, i.e., "off chart".

In addition to eye charts, there are other tests that can be used to measure retinal or visual function but most of these measure aspects of the retina or vision that are not deemed clinically meaningful. For example, non-invasive imaging can be used to measure the thickness of the retina before and after treatment, but that measure is not deemed "clinically meaningful." The Salisbury Eye Evaluation study measures reading rates in individuals with or without glaucoma on a computer screen and correlates reading speed and disease progression. There are a number of different reading charts that have been described, including the MNREaAD chart, Radner reading charts, and International Reading Speed Texts. The Radner reading chart is a visual acuity test in which the text in different cards is displayed with different sizes. The Radner test uses standardized language and is administered with hand-held cards. The Radner test is cumbersome to administer as the tester must juggle various activities simultaneously such as holding the test cards, assuring that that the distances are maintained between the card and the reader's eyes, presenting the cards, writing down the answers, and scoring the responses. There is thus likely to be variability in terms of the distance of the card form the subject's face, angle of the card presented to the subject, and the movement of the card as the clinician writes down the responses. In the MNREaAD reading test and the Radnor Reading test, the size of the print decreases as the test proceeds, aiming to identify the visual acuity of the patient, not the ease of reading. The Colenbrander mixed contrast card set displays individual letters (not text) with high contrast on the left and low contrast on the right. Because the letters are bunched together on the Colenbrander cards, there is little effect of peripheral visual field deficits on the performance. Further, this test suffers from the same problems as the Radner test in that it is hand-held and there are no controls on the level of illumination. This test does not evaluate the speed or accuracy of reading passages, i.e., it does not reflect reading skills.

When peripheral vision is impaired or lost, it becomes very difficult for the individual to move his/her eyes from the end of one line of text to the beginning of the succeeding line of text. This slows down the reading speed and reduces reading accuracy. Reading speed and accuracy are also impaired due to disease processes due to decreased light perception and contrast sensitivity. The reading tests that are currently available concentrate on visual acuity, i.e., foveal function only. However, there is no test on the market that incorporates measures of brightness and contrast and also reflects the effects of peripheral visual field loss.

What is needed in the art is a more reliable, sensitive, rapid, reproducible and informative set of data relating to an activity (reading) that contributes enormously to independence, knowledge accumulation, security, social interactions, and personal fulfillment.

SUMMARY OF THE INVENTION

In one aspect, a method for examining the vision of a subject is provided and includes (i) the subject reading a first passage of text on a screen, wherein the text is displayed on the screen at high image contrast, high illumination, or a combination thereof, (ii) the subject reading a second passage of text on the screen, wherein the text is displayed on the screen at low image contrast, low illumination, or a combination thereof, and (iii) scoring results obtained from steps (i) and (ii).

In another aspect, a method for examining the vision of a subject is provided and includes, (i) displaying a first passage of text at high image contrast, high illumination, or a combination thereof, on a screen, wherein the subject reads the first passage of text, (ii) displaying a second passage of text at low image contrast, low illumination, or a combination thereof, on the screen, the wherein the subject reads the second passage of text, and (iii) scoring results obtained from steps (i) and (ii).

In a further aspect, a method for examining the vision of a subject is provided and includes exposing the subject to a flash of light to 'bleach' the photoreceptors and then conducting the reading test as described herein. This method includes measuring the amount of time required for the subject's photoreceptors to recover from the flash sufficiently to permit an adequate performance on the reading test, and associating recovery time with ocular disease, ocular disease progression or the efficacy of therapy for ocular disease.

In a further aspect, a method for monitoring vision loss in a subject having an ocular disease is provided and includes (i) the subject reading a first passage of text on a screen, wherein the text is displayed on the screen at high image contrast, high illumination, or a combination thereof, (ii) the subject reading a second passage of text on the screen, wherein the text is displayed on the screen at low image contrast, low illumination, or a combination thereof, and (iii) scoring the results of steps (i) and (ii). One embodiment further comprises performing the 'bleach' test described above in conjunction with this method.

In still another aspect, a method for monitoring treatment of an ocular disease is provided and includes (i) treating a subject for vision loss related to the disease, (ii) the subject reading a first passage of text on a screen, wherein the text is displayed on the screen at high image contrast, high illumination, or a combination thereof, (iii) the subject reading a second passage of text on the screen, wherein the text is displayed on the screen at low image contrast, low illumination, or a combination thereof, and (iv) scoring the results of steps (ii) and (iii). One embodiment further comprises performing the 'bleach' test described above in conjunction with this method.

In yet a further aspect, a method for monitoring treatment of an ocular disease is provided and includes (i) treating a subject for vision loss related to the disease, (ii) displaying a first passage of text at high image contrast, high illumination, or a combination thereof, on a screen, wherein the subject reads the first passage of text, (iii) displaying a second passage of text at low image contrast, low illumination, or a combination thereof, on the screen, wherein the subject reads the second passage of text, and (iv) scoring results obtained from steps (ii) and (iii). In one embodiment, the treatment includes gene therapy. One embodiment further comprises performing the 'bleach' test described above in conjunction with this method.

In another aspect, a method for treating a subject for an ocular disease is provided and includes (i) treating a subject for vision loss related to the disease, (ii) the subject reading a first passage of text on a screen, wherein the text is displayed on the screen at high image contrast, high illumination, or a combination thereof, (iii) the subject reading a second passage of text on the screen, wherein the text is displayed on the screen at low image contrast, low illumination, or a combination thereof, (iv) scoring the results of steps (ii) and (iii), and (v) adjusting the subject's treatment of the disease.

In still a further aspect, a method for treating a subject for an ocular disease is provided and includes (i) treating the subject for vision loss related to the disease, (ii) displaying a first passage of text at high image contrast, high illumination, or a combination thereof, on a screen, wherein the subject reads the first passage of text, (iii) displaying a second passage of text at low image contrast, low illumination, or a combination thereof, on the screen, wherein the subject reads the second passage of text, (iv) scoring the results obtained from steps (ii) and (iii), and (v) adjusting the subject's treatment of the disease.

In yet another aspect, a system for clinical examination of vision system functioning of a subject is provided and includes a first unit configured to display text at varying contrasts and illumination, a second unit configured to receive feedback from the subject, a first processor configured to receive the feedback, and a second processor configured to calculate the number of errors in the feedback and provide a score.

In still a further aspect, a electronic vision testing device is provided and includes (a) code for displaying a first passage of text at high image contrast, high illumination, or a combination thereof, on a screen, (b) code for displaying a second passage of text at low image contrast, low illumination, or a combination thereof on the screen, (c) at least one processing unit for executing the code of (a)-(b), (d) at least one processing unit for storing text entered by a subject, and (e) calculating the score by comparing the number of errors in the subject's text.

In another aspect, an electronic vision testing device is provided and includes at least one processing unit configured to acquire data using a first passage of text displayed at high image contrast, high illumination, or a combination thereof on a screen, acquire data using a second passage of text displayed at low image contrast, low illumination, or a combination thereof, on the screen and calculate a score from the data, wherein the score is the percentage of errors in the text.

In a further aspect, a computer program product, stored on a computer readable medium, is provided and includes instructions for configuring a computer to acquire data using a first passage of text displayed at high image contrast, high illumination, or a combination thereof on a screen by a subject reading the first passage of text, acquire data using a second passage of text displayed at low image contrast, low illumination, or a combination thereof, on the screen by the subject reading the second passage of text, and calculate a score from the data, wherein the score is the percentage of errors in the text.

Other aspects and advantages of the invention will be readily apparent from the following detailed description of the invention.

DETAILED DESCRIPTION OF THE DRAWINGS

DETAILED DESCRIPTION OF THE INVENTION

Figure 1:
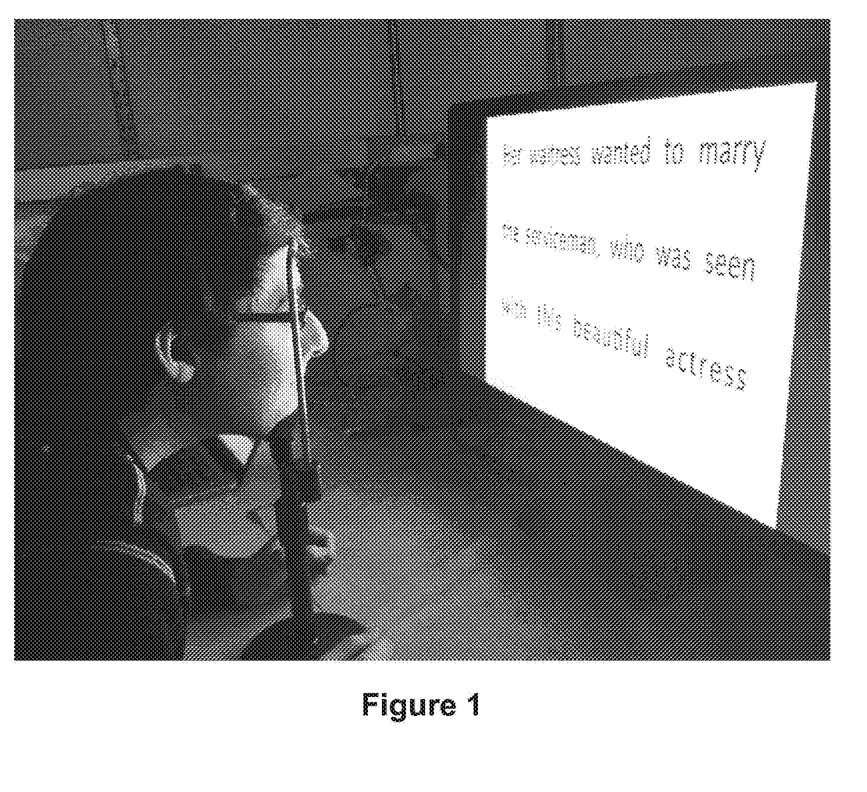
FIG. 1 is a photograph of reading test set-up.

The present invention provides a reading test to measure disease progression and effects of intervention in vision deterioration. The methods described herein are simple, reflect the extent of useful and valued retinal and visual function, non-invasive, quick, sensitive, reproducible, and easy to administer. Thus, the test described in this invention measures the subject's reading speed and accuracy under defined conditions of illumination and contrast. These defined entities are "clinically meaningful" as our ability to read quickly and accurately affect our independence, safety, ability to communicate, and well-being.

The present invention is superior to other vision tests currently utilized in the art. In one embodiment, the methods and vision testing described herein are easy to use by both the subject and clinician. In another embodiment, the methods and vision testing described herein are more quantitative than the reading tests in the art and they provide information that better reflects the individual's ability to navigate and carry out work independently than the other tests. In a further embodiment, the methods and vision testing described herein are significantly faster than the reading tests in the art in large part because of the ease of administering and monitoring the test. The test giver does not have to hold objects and write down answers since both the presentation and recording of answers are carried out digitally. In yet another embodiment, the methods and vision testing described herein are high reproducible. In still a further embodiment, the methods and vision testing described herein provide quantitative readouts which reflect multiple qualitative aspects of vision, i.e., contrast, light sensitivity, visual fields, visual acuity.

The reading test may be used to measure the natural progression of a large number of blinding diseases as well as to assess efficacy after experimental or therapeutic interventions. Accordingly, the vision test permits evaluating and/or measuring a number of vision parameters. In one embodiment, the vision test evaluates and/or measures visual acuity, field of vision, light sensitivity, or contrast sensitivity of the subject. The phrase "visual acuity" as used herein refers to the acuteness or clearness of a subject's vision. "Field of vision" refers to the horizontal, vertical, and/or diagonal extent to which a subject can visually perceive an object. "Contrast sensitivity" describes the ability a subject to visually distinguish between bright and dim components of an image or text.

The test does not require high level cognitive or developmental function. Thus, it can be used with school-age children, i.e., under the age of 18, all of the way through adulthood.

The results of the current methods and vision testing described herein will be useful for correlating reading speed and/or recovery of photoreceptors from exposure to the 'bleaching' effects of a flash of light as a function of time with disease progression. However, because the current methods and testing also incorporate multiple aspects of vision, i.e., visual fields, brightness, or contrast, it will reflect changes in an reading, which is critical to independence, safety, and the ability to function at work and at home. Further, results of this test will reflect the effects of intervention on different specific aspects of visual perception. The results may correlate with those of other visual test paradigms that isolate particular aspects of vision (contrast, for example) and are not recognized as revealing "clinically meaningful" outcomes of an intervention.

Definitions

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

A "subject" or "patient" as used herein is a human. In one embodiment, the subject has a vision impairment or loss. In another embodiment, the vision of the subject is worse than 20/20, e.g., 20/25, 20/32, 20/40, 20/50, /60, 20/80, 20/100, 20/126, 20/160, or 20/200. In a further embodiment, the subject has peripheral-to-central vision loss, central-to-peripheral vision loss, cone-rod photoreceptor degeneration, or rod-cone photoreceptor degeneration/vision loss or combinations thereof.

The subject's vision loss may be due to an injury. In one embodiment, injuries which would cause vision loss include, without limitation, light toxicity, blunt force injury, chemical injury, drug toxicity, radiation damage, or combinations thereof.

The subject's vision loss may alternatively be due to a disease. As used herein, "disease", "disorder" and "condition" are used interchangeably, to describe any medical condition which is linked to a loss of vision in a subject. In one embodiment, the disease is genetic. In another embodiment, the disease is contracted by the subject. In a further embodiment, the disease results in peripheral-to-central loss of vision. In yet another embodiment the disease results in central-to-peripheral vision loss. In still a further embodiment, the disease results in cone-rod photoreceptor degeneration. In another embodiment, the disease results in rod-cone photoreceptor degeneration/vision loss. In still a further embodiment, the disease is systemic with ocular manifestations. In yet another embodiment, the disease is choroideremia, glaucoma, retinitis pigmentosa, diabetic retinopathy, retinopathy of prematurity, sickle cell retinopathy, ocular vein occlusion, Stargardt disease, Leber's congenital amaurosis, endophthalmitis, viral retinitis, pattern dystrophy, cone-rod dystrophy, rod-cone dystrophy, gyrate atrophy, age-related macular degeneration, retinoblastoma, uveitis, retinovascular disease, retinal detachment, lysosomal storage disease, glycogen storage disease, disorders of collagen, mucolipodoses, dystrhyroid eye disease, retinal artery embolism, blue cone monochromacy, or Norrie's disease.

By "bleach" is meant the temporary blinding effect on the photoreceptors caused by exposure to sudden bright light.

The term "clinician" as used herein includes a medical researcher, doctor, physician such as an ophthalmologist, physician's assistant, nurse, mental health professional, optometrist, or other medical professional, the terms being used interchangeably. The clinician is capable of evaluating the vision of a subject as described herein.

Unless defined otherwise in this specification, technical and scientific terms used herein have the same meaning as commonly understood by one of ordinary skill in the art and by reference to published texts, which provide one skilled in the art with a general guide to many of the terms used in the present application.

The Reading Material

The reading material is standardized. In one embodiment, language construction is standardized. In another embodiment, word length such as syllables, i.e., 1, 2, 3, 4, 5, or more syllables is standardized. In a further embodiment, number of words, i.e., 1, 2, 3, 4, 5, 6, 7, 8, 9, 10, 11, 12, 13, 14, 15, 16, 17, 18, 19, 20 or more is standardized. In still another embodiment, the positions of the words are standardized such that there at least one independent clause and at least one subordinate clause. In yet a further embodiment, lexical difficulty and/or syntactical complexity is standardized such that the segment is at the appropriate grade level such as an approximately $6^{th}$ grade level. By doing so, changes in reading performance are not due to text characteristics. The reading material is available in any written language known in the world. In one embodiment, the reading material is in English. In one embodiment, the reading material could be identical to that used in the Radnor test.

The text utilized in the vision tests contain letters, numbers, or symbols or shapes and may be any typeface suitable for performing the vision text. The text may be any color which may be read by the subject. In one embodiment, the text is black or white. In another embodiment, the text is a color other than black or white, i.e., red, orange, yellow, green, blue, indigo, violet, or shades or combinations there between. The text may optionally contain optotypes, i.e., variable sized type, and/or have constant geometric proportions such as character height, width, depth, boldness, and/or italics.

The typeface of the text may be selected by the administered clinician. In one embodiment, the typeface of the text is selected from, without limitation, serif, sans-serif, semi-serif, monospace, script, calligraphic, handwriting, blackletter, non-latin, unicode, dingbat/symbol, display/decorative font, or simulation/mimicry. In another embodiment, the typeface of the text is a sans-serif font.

The sans-serif font may be selected from, without limitation, Abadi, Agency FB, Akzidenz-Grotesk, Andalé Sans, Antique Olive, Aptifer, Arial, Arial Unicode MS, Avant Garde Gothic, Avenir, Bank Gothic, Barmeno, Bauhaus, Bell Centennial, Bell Gothic, Benguiat Gothic, Berlin Sans, Beteckna, Blue Highway, Brandon Grotesque, Cabin, Cafeteria, Calibri, Casey, Century Gothic, Charcoal, Chicago, Clearface Gothic, Clearview, Co Headline, Co Text, Compacta, Corbel, DejaVu Sans, DIN, Dotum, Droid Sans, Dyslexie, Ecofont, Eras, Espy Sans, Eurocrat, Eurostile, FF Dax, FF Meta, FF Scala Sans, Fira Sans, Flama, Folio, Formata, Franklin Gothic, FreeSans, Frutiger, Futura, Geneva, Gill Sans, Gotham, Haettenschweiler, Handel Gothic, Hei, Helvetica, Helvetica neue, Highway Gothic, Hiroshige Sans, Hobo, Impact, Industria, Interstate, Johnston/New Johnston, Kabel, Lato, ITC Legacy Sans, Lexia Readable, Liberation Sans, Linux Biolinum, Lucida Sans, Lydian, Meiryo, Microgramma, Modern, Motorway, MS Sans Serif, Museo Sans, Myriad, Neutraface, Neuzeit S, News Gothic, Nimbus Sans L, Nina, Open Sans, Optima, Parisine, Pricedown, Prima Sans, PT Sans, Rail Alphabet, Revue, Roboto, Rotis Sans, Segoe UI, Sherbrooke, Skia, Source Sans Pro, Souvenir Gothic, ITC Stone Sans, Syntax, Tahoma, Template Gothic, Thesis Sans, Tiresias, Trade Gothic, Transport, Trebuchet MS, Trump Gothic, Twentieth Century, Ubuntu, Univers, Vera Sans, Verdana, or Virtue font.

The serif font may be selected from, without limitation, Adobe Jenson, Adobe Text, Albertus, Aldus, Alexandria, Algerian, American Typewriter, Antigua, Arno, Aster, Aurora, Baskerville, Bebas, Bell, Belwe Roman, Bembo, Berkeley Old Style, Bernhard Modern, Bodoni, Book Antigua, Bookman, Bordeaux Roman, Bulmer, Caledonia, Californian FB, Calisto MT, Cambria, Capitals, Cartier, Caslon, Catull, Centaur, Century Old Style, Century Schoolbook, Chaparral, Charis SIL, Charter, Cheltenham, Clearface, Cochin, Colonna, Computer Modern, Concrete Roman, Constantia, Cooper Black, Copperplate Gothic, Corona, DejaVu Serif, Didot, Droid Serif, Ecotype, Elephant, Emerson, Espy Serif, Excelsior, Fairfield, FF Scala, Footlight, FreeSerif, Friz Quadrata, Garamond, Gentium, Georgia, Gloucester, Granjon, Heather, Hercules, High Tower, Hiroshige, Hoefler, Humana Serif, Imprint, Ionic No. 5, ITC Benguiat, Janson, Jenson, Joanna, Korinna, Kursivschrift, Legacy Serif, Lexicon, Liberation Serif, Linux Libertine, Literaturnaya, Lucida Bright, Melior, Memphis, Miller, Minion, Modern, Mona Lisa, Mrs Eaves, MS Serif, New York, Nimbus Roman, NPS Rawlinson Roadway, OCR A Extended, Palatino, Perpetua, Plantin, Playbill, Poor Richard, Primer, Renault, Requiem, Roman, Rotis Serif, Sabon, Seagull, Sistina, Souvenir, STIX, Stone Informal, Stone Serif, Sylfaen, Times New Roman, Torino, Trajan, Trinité, Trump Mediaeval, Utopia, Vale Type, Vera Serif, Versailles, Wanted, Weiss, Wide Latin, Windsor, or XITS.

The slab serif font may be selected from, without limitation, Alexandria, American Typewriter, Apex, Archer, Athens, Candida, Cholla Slab, City, Clarendon, Concrete Roman, Courier, Egyptienne, Guardian Egyptian, Ionic No. 5, Lexia, Lubalin Graph, Memphis, Museo Slab, Nilland, Rockwell, Schadow, Serifa, Skeleton Antique, Sreda, Stymie, or Tower.

The semi-serif font may be selected from, without limitation, Amsterdam Old Style, Divona, Nyala, Portobello, Rotis Semi Serif, or Tema Cantante.

The monospace font may be selected from, without limitation, Andale Mono, Anonymous and Anonymous Pro, Arial Monospaced, BatangChe, Bitstream Vera, Consolas, Courier, DejaVu Sans Mono, Droid Sans Mono, Everson Mono, Fedra Mono, Fixed, Fixedsys, HyperFont, Inconsolata, KaiTi, Letter Gothic, Liberation Mono, Lucida Console, Lucida Sans Typewriter, Lucida Typewriter, Menlo, MICR, Miriam Fixed, Monaco, Monofur, Monospace, MS Gothic, MS Mincho, Nimbus Mono L, OCR-A, Orator, Ormaxx, PragmataPro, Prestige Elite, ProFont, Proggy programming fonts, SimHei, SimSun, Small Fonts, Source Code Pro, Sydnie, Terminal, Tex Gyre Cursor, Trixie, Ubuntu Mono, UM Typewriter, Vera Sans Mono, or William Monospace.

The script font may be selected from, without limitation, Balloon, Brush Script, Choc, Dom Casual, Dragonwick, Mistral, Papyrus, Segoe Script, Tempus Sans, or Utopia. Additional script fonts that may be utilized include Alecko, Cinderella, Coronet, Cupola, Curlz, Magnificat, Script, Stone or Informal.

The calligraphic font may be selected from, without limitation, Amazone, American Scribe, AMS Euler, Apple Chancery, Aquiline, Aristocrat, Bickley Script, Civitype, Codex, Edwardian Script, Forte, French Script, ITC Zapf Chancery, Kuenstler Script, Monotype Corsiva, Old English Text MT, Palace Script, Park Avenue, Scriptina, Shelley, Volante, Vivaldi, Vladimir Script, or Zapfino.

The handwriting font may be selected from, without limitation, Andy, Ashley Script, Cézanne, Chalkboard, Comic Sans MS, Dom Casual, Eyadish, Fontoon, Irregularis, Jefferson, Kristen, Lucida Handwriting, Rage Italic, Rufscript, Scribble, Soupbone, or Tekton.

The blackletter font may be selected from, without limitation, American Text, Bastard, Breitkopf Fraktur, Cloister Black, Fette Fraktur, Fletcher, Fraktur, Goudy Text, Lucida Blackletter, Old English Text, Schwabacher, or Wedding Text.

The non-latin font may be selected from, without limitation, Aegyptus, Aharoni, Aisha, Alfarooq, Amienne, Aparajita, Arial, Batak Script, Calibri, Chandas, Embria, Estrangelo Edessa, Gadugi, Grecs du roi, Hanacaraka, Japanese Gothic, Jomolhari, Kochi, Koren, Lontara Script, Maiola, Malgun Gothic, Meiryo, Microsoft Himalaya, Microsoft JhengHei, Microsoft YaHei, Minchō, Ming, Mona, MS Gothic, MV Boli, Myanmar, Nastaliq Navees, Neacademia, Perpetua Greek, Porson, Samman, Segoe UI Symbol, Shonar Bangla, Shruti, SimSun, Sundanese Unicode, Sutturah, Sylfaen, Tai Le Valentinium, Tahoma, Tengwar, Tibetan Machine Uni, Tunga, Vrinda, Wadalab, or Wilson Greek.

The Unicode font may be selected from, without limitation, Alphabetum, Arial Unicode MS, Batang and Gungsuh, Bitstream Cyberbit, Bitstream Vera, Charis SIL, ClearlyU, Code2000, DejaVu, Doulos SIL Everson Mono, Fallback font, Fixedsys Excelsior, Free UCS Outline Fonts aka FreeFont, Gentium, GNU Unifont, Georgia, Ref Gulim/New Gulim and Dotum, Junicode, LastResort, Lucida Grande, Lucida Sans Unicode, MS Gothic, MS Mincho, Nimbus Sans Global, Squarish Sans CT v0.10, STIX, Symbola, Titus Cyberbit Basic, Verdana Ref, Y.OzFontN, or XITS.

The dingbat/symbol font may be selected from, without limitation, Apple Symbols, Asana-Math, Blackboard bold, Bookshelf Symbol 7, Braille, Cambria Math, Commercial Pi, Computer Modern, Corel, Erler Dingbats, HM Phonetic, Lucida Math, Marlett, Mathematical Pi, Morse Code, OpenSymbol, RichStyle, Symbol, Webdings, Wingdings, or Zapf Dingbats.

The display/decorative font may be selected from, without limitation, Abracadabra, Ad Lib, Allegro, Andreas, Arnold Bocklin, Astur, Balloon Pop Outlaw Black, Banco, Bauhaus, Beat, Braggadocio, Broadway, Caslon Antique, Cooper Black, Curlz, Ellington, Exablock, Exocet, FIG Script, Forte, Gabriola, Gigi, Harlow Solid, Harrington, Horizon, Jim Crow, Jokerman, Juice, Lo-Type, Loyolliams, Magneto, Megadeth, Neuland, Peignot, Ravie, San Francisco, Showcard Gothic, Snap, Stencil, Umbra, Westminster, Willow, or Windsor.

A "passage of text" as used herein refers to text at one specific contrast and a specified illumination. The text may be a single letter, word, sentence, or paragraph including two or more sentences. The text may be displayed on one screen or on separate screens. In one embodiment, a first passage of text is at high contrast and/or high illumination. In another embodiment, a second passage of text is at low contrast and/or low illumination.

The difficulty of the text depends on the subject. In one embodiment, the difficulty of the text is proportional to the reading ability of the subject. In another embodiment, the difficulty of the text exceeds the reading ability of the subject. In a further embodiment, the difficulty of the text is lower than the reading ability of the subject. The text in the sets may be varying difficulty. In one embodiment, all of the text in each set has the same difficulty level. In another embodiment, different paragraphs in each passage of text vary in difficulty.

Vision Test Set-Up

The vision test described herein may be performed using varying arrangements of hardware. As a first component, a screen is required to visualize the reading text described above. Any screen which is capable of displaying text at varying illumination and contrast may be utilized and selected by one skilled in the art. The resolution of the screen may be determined by the clinician administering the test and may range from low to high resolution monitors. In one embodiment, the screen is a high resolution monitor. In another embodiment, the resolution of the monitor is about 1280×720 or greater.

The screen may be any flat surface which is capable of sustaining an image. In one embodiment, the screen is a digitized monitor, wall, paper, fabric, among others. In another embodiment, the screen is a digitized monitor such as a computer monitor, TV monitor, Snellen chart, projection screen, projection goggles, or an optical head-mounted display such as Google glass. The computer or TV monitor may be a liquid crystal display monitor, cathode ray tube monitor, light emitting diode monitor, plasma monitor, or rear projection TV monitor, among others. The Snellen chart may be selected by those skilled in the art and is traditionally printed with separate lines (1-11) of block letters selected from among C, D, E, F, H, K, L, N, O, P, R, T, U, V, or Z. In one embodiment, the monitor is wall-mounted. In another embodiment, the monitor is mounted on a table. In a further embodiment, the monitor is transportable.

The subject is positioned horizontally in front of the screen such that the reading text may be unobstructively visualized. In one embodiment, the subject is positioned such that the text on the screen is not blurry due to distance. In another embodiment, the subject is positioned at least about 0.5 m from the screen. In a further embodiment the subject is positioned about 0.5 to about 4 m, i.e., 0.5, 1, 1.5, 2, 2.5, 3, 3.5, or 4 m, or fractions or ranges there between, from the screen.

The screen is positioned vertically to provide the optimal ease of reading by the subject. The subject is also positioned to minimize variability. In one embodiment, the subject is positioned at eye level to the center of the screen. In another embodiment, the subject is positioned such that the highest and lowest lines of text are less than an about ±45° angle, i.e., 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 9, 8, 7, 6, 5, 4, 3, 2, 1, or 0°, or fractions or ranges there between, from the center of the screen. In a further embodiment, the subject is positioned such that the highest and lowest lines of text are at an about 0 to about 20° angle of integers, fractions, or ranges there between, from, the center of the screen. Such positioning may be accomplished using seating media which permit the upward and downward movement of the subject such as an adjustable chair or stool.

Desirably, the subject is positioned such that movement of the subject's head is minimal if at all. In one embodiment, the vision test is performed in the absence of subject movement. In another embodiment, the head of the subject is fixed in one position. In a further embodiment, the subject's chin is positioned in a chin rest or strap. The chin is optionally secured to the chin rest using techniques known to those skilled in the art.

The subject performs the vision test in the absence of pupil dilation. However, dilation of the pupils may be performed as determined by the attending clinician. If corrective lenses are prescribed for the subject, the same may be worn. Such corrective lens(es) include glasses or contact lenses.

Optional Tests and/or Reagents

Additional tests may be utilized in combination with the vision tests described herein. Examples of additional tests include, without limitation, applanation tonometry (using local anesthetic drops and a dye to measure pressure), corneal and retinal topography, fluorescein angiogram (using fluorescein to diagnose circulation, swelling, leaking, or abnormal blood vessels in the eyes), dilated pupillary exam, refraction (determining eyeglasses prescription using a phoropter), slit-lamp exam (using a microscope to shine an adjustable beam of light shaped like a small slit on the eye), non-contact tonometry (using a tonometer to measure the pressure in the eye), ultrasound (using sound waves to provide a picture of the eye's internal structure), visual acuity, visual field (measures peripheral vision), color vision tests, keratometry, cycloplegic refraction, amsler grid, gonioscopy, corneal pachymetry, scanning laser polarimetry, electrooculography, electroretinography, or ultrasound biomicroscopy, among others.

Optional 'Bleaching' Step

In another aspect of the methods, systems and apparatus described herein, an optional 'bleaching' step, or means for accomplishing and measuring the effects of an optional bleaching step are further embodiments. In one embodiment, a bleaching step is combined with the vision (reading) test. In the optional step, the subject's eye(s) are exposed to a brief flash of light of a defined illuminance of suitable intensity and duration to temporarily bleach or blind the photoreceptors without causing any permanent damage. Such suitable illuminations and durations may be selected by the person of skill in the art based upon the condition of the subject's photoreceptor. This exposure occurs immediately before the reading text is displayed on the screen. After the subject's photoreceptor's have recovered from the bleaching effect so that the subject can read the text, a score is calculated reflecting the speed/accuracy of performance of the reading test as a function of the amount of time it takes for the individual's retinas to recover from the flash (i.e. to recover from the 'bleach' of photoreceptors in the subject's eyes) to enable reading. The 'bleach' test can be carried out after exposure to flashes of different intensity/wavelengths and duration and under different conditions of text presentation such as using low/high image contrast, low/high illumination, or a combination thereof on a screen. This test is conducted before and after a therapeutic intervention in order to determine if the intervention has any effect on the time required for the subject to recover from exposure to the light flash. The test is also useful to monitor disease progression (i.e., to determine if the recovery time from the 'bleach effect' on the retina lengthens or decreases as the disease progresses or as therapeutic intervention is continued).

Implementation of the Vision Test

The methods described herein for examining the vision of a subject may be monitored by one skilled in the art including the attending clinician. The subject reads the text that is displayed on the screen. In one embodiment, neither eye is covered during the test, i.e., the eyes are evaluated simultaneously. In another embodiment, only one eye at a time is examined. If only one eye is examined, this may be accomplished by covering the contralateral eye, i.e., eye on the other side. One eye may be covered using a hand, cloth, patch, occlude, or the like. In another embodiment, the subject's eyes are dilated. In another embodiment, the subject's eye(s) are not dilated. In another embodiment, the subject wears optical correction during the test. In still another embodiment, the subject does not wear optical correction.

In one embodiment, the subject orally reads the text. The subject's reading is recorded using media known in the art. In another embodiment, the subject reads the text by using sign language utilized by the hearing impaired. In the latter case, an interpreter enters the text covered by the sign language into the processor as described below.

One or more passages of text may be displayed on the screen serially or simultaneously for reading by the subject. In one embodiment, two or more passages are displayed on a separate slide. In another embodiment, at least one passage of text is at a different contrast and illumination than the other passages of text displayed in the vision test. In a further embodiment, at least two passages of text are displayed at separate contrasts and illuminations. In another embodiment, three or more passages of text are displayed at three separate contrasts and illuminations.

One step of the method includes the subject reading a first passage of text on a screen at high image contrast and/or high illumination. In one embodiment, the text has a high image contrast and high illumination. In a further embodiment, the text has a low image contrast and low illumination. In another embodiment, the text has a low image contrast and high illumination. In still a further embodiment, the text has a high image contrast and low illumination. In a further embodiment, the first passage of text is a low illumination and would increase in illumination as the vision text progresses. In another embodiment, the illumination of the text is kept constant and the contrast is varied from the lowest to the highest contrast. In a further embodiment, the contrast of the text is kept constant and the illumination of the text is varied from the lowest to the highest illumination. In yet another embodiment, the text starts at a low illumination and high contrast, the illumination is increased while keeping the contrast constant, and finally increasing the illumination the maximum, all while keeping the contrast constant. In still a further embodiment, the text starts at a low contrast and high illumination, the contrast is increased while the high illumination is held constant, and finally the contrast is increased to the maximum, while keeping the contrast constant. In another embodiment, the text starts a low illumination and low contrast and the illumination and contrast is progressively increased until each is at the highest contrast and illumination, i.e., 100%.

In one embodiment, the first passage of text includes a first text displayed on the screen, followed by a second text displayed on the same screen. The first text is removed from the screen prior to display of the second text. Three or more text may be independently displayed on the screen, following removal of the second text. In one embodiment, two or more text passages are independently displayed on the screen. In another embodiment, 2 to about 3, 4, 5, 6, 7, 8, 9, 10, 11, 12, 13, 14, 15, 16, 7, 18, 19, 20, 21, 22, 23, 24, 25, 26, 27, 28, 29, 30, 31, 32, 33, 34, 35, 36, 37, 338, 39, 40, 41, 42, 43, 45, 46, 47, 48, 49, or 50, or fractions or ranges there between, sections of text are, independently displayed, on the screen. In a further embodiment, about 24 sections of text at high illumination and/or high contrast are independently displayed on the screen. In still another embodiment, about 30 sections of text at high illumination and/or high contrast are independently displayed on the screen.

As used herein, the term "illumination" is used to refer to the luminous intensity which is emitted from a particular area of the screen. In one embodiment, "high illumination" of the text or images described herein are about 200 to about 500 $cd/m^2$, i.e., 200, 210, 220, 230, 240, 250, 260, 270, 280, 290, 300, 310, 320, 330, 340, 350, 460, 470, 480, 490, 400, 410, 420, 430, 440, 450, 460, 470, 480, 490, 500, or integers, fractions or ranges there between. In another embodiment, "high illumination" is about 200 to about 350 $cd/m^2$. In a further embodiment, "low illumination" is about 1 to about 50 $cd/m^2$, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 $cd/m^2$ or fractions or ranges there between.

The term "contrast" as used herein is determined by the difference in the color and brightness of the image or text in the same field of view compared to the background color/brightness and is measured by percentage. The contrast may range from high to low. By way of example, a high contrast includes black letters on a white background. In one embodiment, a high contrast is about 1.7 to about 2.25 log units, i.e., 1.7, 1.75, 1.8, 1.85, 1.9, 1.95, 2, 2.05, 2.1, 2.15, 2.2, or 2.25 log units, or fractions or ranges there between. By way of example, low contrast may include grey letters on a slightly gray background. In one embodiment, a low contrast includes saturation below the background contrast. In another embodiment, a low contrast is up to 1.35, i.e., 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.0, 1.01, 1.02, 1.03. 1.04, 1.05, 1.06, 1.07, 1.08, 1.09, 1.0, 1.1, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34 or 1.35, log units or fractions or ranges there between.

Another step of the method includes the subject reading a first passage of text on a screen at low image contrast and/or low illumination. The text may have a low image contrast, low illumination, or low contrast and low illumination. In one embodiment, the first passage of text at low contrast and/or low illumination includes a first text displayed on the screen, followed by a second text displayed on the same screen. The first text is removed from the screen prior to displaying the second text. Three or more texts may be independently displayed on the screen, following removal of the second text. In one embodiment, two or more text passages at low contrast and/or low illumination are, independently, displayed on the screen. In another embodiment, 2 to about 3, 4, 5, 6, 7, 8, 9, 10, 11, 12, 13, 14, 15, 16, 7, 18, 19, 20, 21, 22, 23, 24, 25, 26, 27, 28, 29, 30, 31, 32, 33, 34, 35, 36, 37, 338, 39, 40, 41, 42, 43, 45, 46, 47, 48, 49, or 50, or fractions or ranges there between, sections of text are, independently displayed, on the screen. In a further embodiment, about 24 sections of text at low illumination and/or low contrast are independently displayed on the screen. In still another embodiment, about 30 sections of text at low illumination and/or low contrast are independently displayed on the screen.

In another embodiment the level of contrast (or brightness) is determined through the percent reduction in brightness (from 100% brightness and contrast, respectively).

The text is advanced on the screen using techniques in the art. In one embodiment, a button is pressed, which button is connected to the monitor. The connection may be physically or wirelessly connected to the screen. In another embodiment, a button on a separate keypad or on the screen, i.e., a computer generated button, is pressed. The computer generated button may be displayed using technologies known in the art such as a touchscreen. In a further embodiment, the text may be advanced by voice-controlled software. The subject, clinician, or a third party may be responsible for advancing the text.

Results from the Vision Test

Once the subject has completed the reading portion of the test, the results are interpreted to reflect reading speed and accuracy. The interpretation of the data is completed using a baseline score. The term "baseline score" as used herein refers to the score of the vision test in which the subject first notices a vision loss, i.e., at disease onset or diagnosis of the disease. The baseline score may be compared with future scores in order to track disease progression and/or the effects of disease intervention. In one embodiment, the baseline score is the score of the first vision test described herein performed by the subject. This baseline score is utilized to determine if a subject's vision worsens. In one embodiment, a higher baseline score correlates to an improvement in vision. In another embodiment, a lower baseline score correlates to worsening of vision. In another embodiment, the baseline score takes into account the effects of the bleaching step. In one embodiment, the baseline score taken when the bleaching and vision tests are combined involves correlating time of recovery from the bleaching effect with accuracy of performance in the reading portion of the test and determines the association if any, of such combined scores with ocular disease/vision loss or therapeutic efficacy.

The results from the vision test performed at the varying illumination and contrast is then determined, i.e., and an overall score is calculated. The overall score is determined by calculating a score from the high illumination and/or high contrast portion of the test and a score from the low illumination and/or low contrast vision portion of the test.

To calculate the reading score for the high illumination/ high contrast, the number of words in the text that is read incorrectly at high illumination and/or high contrast is counted. This number is then divided by the total number of words in the text at the same high illumination and multiplied by 100 to provide a percentage. Similarly, to calculate the reading score at low illumination/low contrast, the number of words in the text that is read incorrectly in the text at lower illumination and low contrast by the subject is counted. This number is then divided by the total number of words in the text at the same low illumination and/or low contrast and multiplied by 100 to provide a percentage.

The high illumination/contrast and low illumination/contrast scores are then averaged to provide a cumulative score. In one embodiment "scoring" comprises compiling the results of steps (i) and (ii) as defined herein, quantitating the compiled results, and weighting the quantitated results to provide a cumulative score. This cumulative score provides insight regarding the accuracy and reading speed of the subject.

Alternatively, the reading score for all of the text, regardless if the text is read at high illumination, high contrast, low illumination, and/or low contrast is calculated. The number of words in all the text that is read incorrectly is counted. This number is then divided by the total number of words in all of the text and multiplied by 100 to provide a percentage which is the score.

The scores can also be weighted based on additional variables. In one embodiment, the scores are weighted against mistakes that the subject makes during reading each portion of the text. In a further embodiment, the scores are weighted against words stated by the subject but which are not in the written text. In another embodiment, the scores are weighted against whether the subject back-tracks to re-read part of the passage. In still a further embodiment, the scores are weighted against the amount of time that it takes for each subject to read each portion of the text. In yet another embodiment, the time includes any pauses that are made by the subject. In a further embodiment, the time lacks any pauses that are made by the subject and includes only time that the subject is speaking.

Application of the Vision Test

The vision test described herein has broad sweeping applicability and usefulness in the art. Simply put, the vision test is useful both qualitatively and quantitatively in methods for monitoring vision loss in a subject having an ocular disease. The vision loss of the subject may result from a physical injury to the eye or a genetic disorder resulting from an ocular disease as set forth above. In one embodiment, the vision loss being analyzed is peripheral-to-central loss of vision, central-to-peripheral vision loss, cone-rod photoreceptor degeneration, or rod-cone photoreceptor degeneration/vision loss. In another embodiment, the vision loss is due to choroideremia, glaucoma, retinitis pigmentosa, diabetic retinopathy, retinopathy of prematurity, sickle cell retinopathy, ocular vein occlusion, Stargardt disease, Leber's congenital amaurosis, endophthalmitis, viral retinits, pattern dystrophy, cone-rod dystrophy, rod-cone dystrophy, gyrate atrophy, age-related macular degeneration, retinoblastoma, uveitis, retinovascular disease, retinal detachment, lysosomal storage disease, glycogen storage disease, disorders of collagen, mucolipodoses, dystrhyroid eye disease, retinal artery embolism, blue cone monochromacy, or Norrie's disease.

Monitoring of the subject's vision may be performed for any length of time as determined by the treating clinician. For example, the subject's vision loss may be performed at specific time periods, certain points in the treatment regimen, or on demand as required to assess vision loss.

The vision tests are also useful in determining an initial treatment of an ocular disease, monitoring treatment of an ocular disease, and/or altering a treatment of an ocular disease. Any ocular treatments may be monitored and include, without limitation, gene therapy, cell therapy, pharmaceutical therapy, or device intervention.

The results of the vision test may result in the clinician treating the subject with a pharmaceutical therapy or changing the particular pharmaceutical therapy. One skilled in the art would readily be able to select a suitable pharmaceutical therapy for a subject with vision loss. The selection of the suitable pharmaceutical therapy depends on the cause of the vision loss, subject's age, weight, and other physical attributes, and other factors evaluated by a clinician. In one embodiment, the pharmaceutical therapy includes administration of a pharmaceutical drug. In a further embodiment, the pharmaceutical therapy may be topical, intravitreal, intravenous, or oral. In another embodiment, the pharmaceutical drug may affect growth or well-being of ocular cells. In still a further embodiment, the pharmaceutical drug affects ocular neurotrophic factors. In another embodiment, the pharmaceutical drug includes, without limitation, acetazolamide, apraclonidine HCl, betaxolol HCl, bimatoprost, brimonidine tartrate, brinzolamide, carbachol, dorzolamide HCl, latanoprost levobunolol HCl, methazolamide, metipranolol, pilocarpine HCl, timolol maleate, timolol hemihydrate, tafluprost, travaprost, vitamin A, beta-carotene, docosahexaenoic acid, acetazolamide, corticosteroid, calcium channel blocker, lutein, zeaxanthin, valproic acid, aspirin, anti-inflammatory agent such as a corticosteroid (dexamethasone, fluorometholone, or prednisolone acetate), warfarin, heparin, alteplase, fibrinolytic agent, alteplase, ranibizumab, aflibercept, triamcinolone, bevacizumab, dexamethasone, prednisolone, antibacterial agent (moxifloxacin, chloramphenicol, gentamycin, neomycin, sulfacetamide, tobramycin, bacitracin, erythromycin, polymyxin B, or sulfasoxazole), retinoid derivative, anti-neovascular compound, anti-fungal (natamycin), anti-apoptotic factor, vitamin, anti-mitotic agent, vasoconstrictor (phenylephrine, naphazoline, or tetrahydrozoline), anti-infective eye medication, antiviral (idoxuridine, vidarabine, or trifluridine), nonsteroidal anti-inflammatory (flurbiprofen sodium, suprofen, or diclofenac), anesthetic eye medication, or lubricant, among others.

In another embodiment, the results of the vision test may lead the clinician in recommending or altering the gene therapy treatment of the subject. One skilled in the art would readily be able to select suitable gene therapy for a subject with vision loss. Accordingly, the gene therapy may include, without limitation, adeno-associated virus, lentiviral virus, adenovirus, or non-viral gene delivery.

In yet another embodiment, the results of the vision test may result in the clinician treating the subject with cell therapy or changing the cell therapy. One of skilled in the art would be able to select a suitable cell therapy for a subject with vision loss. In one embodiment, the cell therapy may include, without limitation, transplantation of fetal-derived retinal progenitor cells, induced pluripotent stem cells, embryonic stem cells, retinal pigment epithelium cells, or cells encased in a capsule.

In a further embodiment, the results of the vision test may result in the clinician treating the subject with a device intervention or changing the particular device intervention. One skilled in the art would readily be able to select a suitable device intervention for a subject with vision loss. The phrase "device intervention" as used herein refers to a procedure in which an exogenous agent is not administered to the subject. For example, device interventions useful in treating a subject with vision loss include, without limitation, oxygen therapy, surgery, cryotherapy, photocoagulation, diathermy, isovolemic hemodilution, plasmapheresis, retinal neurostimulus chip implant, i.e., a prospthesis, such as the Argus® II implant, and light stimulation unit such as those used in conjunction with optogenetic therapy.

Accordingly, the vision test described herein may be used in methods for treating a subject for an ocular disease. The methods include treating the subject for vision loss related to the disease, performing a vision test as described herein, and implanting and/or adjusting the subject's treatment of the disease.

In one embodiment, a method for examining the vision of a subject is provided and includes (i) the subject reading a first passage of text on a screen, wherein the text is displayed on the screen at high image contrast, high illumination, or a combination thereof, (ii) the subject reading a second passage of text on the screen, wherein the text is displayed on the screen at low image contrast, low illumination, or a combination thereof, and (iii) scoring results obtained from steps (i) and (ii).

In a further embodiment, a method for examining the vision of a subject is provided and includes (i) displaying a first passage of text at high image contrast, high illumination, or a combination thereof on a screen, wherein the subject reads the first passage of text, (ii) displaying a second passage of text at low image contrast, low illumination, or a combination thereof on the screen, wherein the subject reads the second passage of text, and (iii) scoring results obtained from steps (i) and (ii).

In another embodiment, a method for monitoring vision loss in a subject having an ocular disease is provided. The method includes (i) the subject reading a first passage of text on a screen, wherein the text is displayed on the screen at high image contrast, high illumination, or a combination thereof, (ii) the subject reading a second passage of text on the screen, wherein the text is displayed on the screen at low image contrast, low illumination, or a combination thereof, and (iii) scoring the results of steps (i) and (ii).

In still a further embodiment, a method for monitoring treatment of an ocular disease is provided. The method includes (i) treating the subject for vision loss related to the disease, (ii) the subject reading a first passage of text on a screen, wherein the text is displayed on the screen at high image contrast, high illumination, or a combination thereof, (iii) the subject reading a second passage of text on the screen, wherein the text is displayed on the screen at low image contrast, low illumination, or a combination thereof, and (iv) scoring the results of steps (ii) and (iii).

In yet another embodiment, a method for monitoring treatment of an ocular disease is provided. The method includes (i) treating the subject for vision loss related to the disease, (ii) displaying a first passage of text at high image contrast, high illumination, or a combination thereof on a screen, wherein the subject reads the first passage of text, (iii) displaying a second passage of text at low image contrast, low illumination, or a combination thereof on the screen, wherein the subject reads the second passage of text, and (iv) scoring results obtained from steps (ii) and (iii).

In a further embodiment, a method for treating a subject for an ocular disease is provided. The method includes (i) treating the subject for vision loss related to the disease, (ii) the subject reading a first passage of text on a screen, wherein the text is displayed on the screen at high image contrast, high illumination, or a combination thereof, (iii) the subject reading a second passage of text on the screen, wherein the text is displayed on the screen at low image contrast, low illumination, or a combination thereof, (iv) scoring the results of steps (ii) and (iii), and (v) adjusting the subject's treatment of the disease.

In another embodiment, a diagnostic method which would guide treatment of a subject for an ocular disease is provided. The method includes (i) treating the subject for vision loss related to the disease, (ii) displaying a first passage of text at high image contrast, high illumination, or a combination thereof, on a screen, wherein the subject reads the first passage of text, (iii) displaying a second passage of text at low image contrast, low illumination, or a combination thereof on the screen, wherein the subject reads the second passage of text, (iv) scoring the results obtained from steps (ii) and (iii), and (v) adjusting the subject's treatment of the disease.

In yet a further embodiment, visual acuity, field of vision, light sensitivity, and/or contrast sensitivity of the subject is measured.

In a further embodiment, treatment includes gene therapy, pharmaceutical therapy, or device intervention.

In another embodiment, high illumination is about 200 to about 500 $cd/m^2$.

In still another embodiment, high contrast is 0.0 to about 2.25 log units.

In a further embodiment, low contrast is about 1.35 to about 2.25 log units.

In still another embodiment, low illumination is about 1 to about 50 $cd/m^2$.

In yet another embodiment, the disease is choroideremia, glaucoma, retinitis pigmentosa, diabetic retinopathy, retinopathy of prematurity, sickle cell retinopathy, ocular vein occlusion, stargardt disease, Leber's congenital amaurosis, endophthalmitis, viral retinits, pattern dystrophy, cone-rod dystrophy, rod-cone dystrophy, gyrate atrophy, age-related macular degeneration, retinoblastoma, uveitis, retinovascular disease, retinal detachment, lysosomal storage disease, glycogen storage disease, disorders of collagen, mucolipodoses, dystrhyroid eye disease, retinal artery embolism, blue cone monochromacy, or Norrie's disease.

Systems and Devices

The methods described herein are performed by an electronic device. The term "electronic device", as used herein, refers to a computer processor (processing unit) or computer-programmed instrument that generates numerical or graphical data, i.e., code. Therefore, the methods described herein include computer program products which are stored on a computer readable medium. In one embodiment, the computer program product includes instructions for configuring a computer to perform the methods described herein.

The computers and devices discussed herein may be based on the computers and components available in the art. Such components may include, without limitation, a central processing unit including graphics processing units, a chipset including a north bride, a random-access memory, a read-only memory, basic input output system, unified extensible firmware interface, buses, CMOS battery, expansion cards, storage devices, fixed media such as hard disk drives, solid-state drives, disk array controllers, removable media such as USB flash drives or optical discs, input devices such as a mouse, keyboard, touchpads, webcams, microphones, joysticks, or image scanners, or output devices such as printers, speakers, or Braille embossers, or combinations thereof.

The programs utilized to perform the methods described herein may be prepared by those skilled in the art. The programs include executable form or code that the computer can use directly to execute the instructions, i.e., the software. The code used to perform the methods may be converted into an executable file, may be executed with the aid of an interpreter, or may be embedded thereby not requiring human intervention. Two or more computer programs may be utilized to perform the methods and may run independently or simultaneously.

The code described herein may be executed as described above and using techniques in the art. In one embodiment, the devices described herein include at least one processing unit for executing the code.

Accordingly, a system for clinical examination of visual system functioning of a subject is described herein. This system includes a first unit configured to display text at varying contrasts and illumination. In one embodiment, the first unit is configured to project a first passage of text at high illumination and/or high contrast as described above. In a further embodiment, the first unit is configured to project a second passage of text at low illumination and/or low contrast. In another embodiment, the first unit is further configured to project instructions to the subject. In one embodiment, the system contains another unit or one of the first or second units is configured to apply a flash of light prior to the reading test to temporarily 'bleach' the photoreceptors in order to measure recovery time before the subject is capable of reading the text.

The system also includes a second unit configured to receive feedback from the subject. The term "feedback" as used herein refers to the subject's interpretation or representation of the text. In one embodiment, the second unit includes recordable media or voice recognition software to receive oral feedback from the subject. In another embodiment, the second unit includes software which permits entry of the feedback of the subject. The feedback may be entered by the subject, technician, or clinician. Also included in the system is a first processor configured to receive the feedback.

Finally, the system includes a second processor configured to calculate the number of errors in the feedback. The second processor is also configured to provide a score which is the percentage of errors in the data. This processor may be optionally configured to measure the time of recovery from the 'bleaching' test.

The system optionally contains a means for instructing the first unit to project the text. In one embodiment, the means may be a mechanical button adjacent to the first unit and connected to the first unit through a first conduit. In another embodiment, the means may be a computer generated button. The computer generated button is displayed on the first unit using technologies such as a touchscreen.

In one embodiment, a system for clinical examination of vision system functioning of a subject is provided and includes a first unit configured to display text at varying contrasts and illumination, a second unit configured to receive feedback from the subject, a first processor configured to receive the feedback, and, a second processor configured to calculate the number of errors in the feedback and provide a score.

In a further embodiment, an electronic vision testing device is provided. The device includes code for displaying a first passage of text at high image contrast and/or high illumination on a screen. The device also includes code for displaying a second passage of text at low image contrast and/or low illumination on the screen. The device further includes at least one processing unit for executing the code.

In another embodiment, an electronic vision testing device is provided. The device includes at least one processing unit configured to acquire data using a first passage of text displayed at high image contrast and/or high illumination on a screen, acquire data using a second passage of text displayed at low image contrast and/or low illumination on the screen, and calculate a score from the data.

In yet a further embodiment, a computer program product, stored on a computer readable medium, is provided. The product includes instructions for configuring a computer to acquire data using a first passage of text displayed at high image contrast and high illumination on a screen by a subject reading the first passage of text, acquire data using a second passage of text displayed at low image contrast and/or low illumination on the screen by the subject reading the second passage of text, and calculate a score from the data.

In another embodiment, a pupil-tracking device is provided. The device follows the fixation point of the subject and thus provides data on sensitivity of different parts of the eye, i.e., retina, macula, the "preferred retinal locus", among others, eye movements such as presence or amplitude of nystagmus, among others.

EXAMPLES

The following examples are illustrative only and are not intended to limit the present invention.

Example 1

A reading test was performed and permits repeated, sensitive, quick, and accurate measures of reading accuracy and reading speed. The test was performed in a room without any windows and in which the room lights could be completely turned off. The subject (male subject, 25 years of age) sat comfortably in a chair with his chin on the chin rand forehead positioned on the chin rest frame with his eyes approximately 0.3 m distance from a large (31.5 inch diagonal) high resolution LCD monitor with his chin in a chinrest. The subject is positioned so that the center of the LCD monitor screen is at eye level. The subject was tested in an undilated state, with the subject wearing his glasses for his optical correction. The testing was performed one eye at a time by patching the contralateral eye. The right eye was patched first (left eye tested).

The text is displayed to him in the first slide, using Helvetica Neue size 48 font. A sentence from the Radnor reading test is displayed. The sentences are double-spaced and occupy most of the area of the monitor. The subject's left eye is patched (but out of view) so he is using his right eye to read and he reads out loud.

After the subject was in the position, computer-generated black and white images were fed to the high resolution monitor. When the subject was ready and comfortable, the first reading chart was displayed on the monitor. The text was displayed in a large, sans serif font. The subject read the text out loud, keeping his head still and moving only his eyes. The testing was recorded by audio. When the subject completed reading the text, the next text file was displayed and the process is repeated.

The first reading chart included text with high contrast, i.e., saturation above background, and different levels of illumination, starting with the dimmest light first. Each subsequent reading chart had increased brightness going up to the maximum brightness of 250 cd/m$^2$. Levels were presented as a percentage of the maximum brightness level. Levels started with −90% brightness (100% contrast), then to −85% brightness (100% contrast), then −75% brightness (100% contrast), then −50% brightness (100% contrast), then baseline brightness (100% brightness; 250 cd/m$^2$ with 100% contrast.

Next, contrast was altered, keeping brightness constant. The first stimulus was −95% contrast (100% brightness), then −90% contrast (100% brightness), then −75% contrast (100% brightness), then −50% contrast (100% brightness). Finally, both modalities were altered simultaneously, starting with −90% brightness/−95% contrast; then −85% brightness/−90% contrast; then −75% brightness/−75% contrast; then −50% brightness/−50% contrast. Each time the reading chart changed, the clinician said "next" so that the subject knew to read the segment. For each test, a different sentence is displayed so that the subject does not memorize the text. The specific sentence and/or the order of the sentences is changed to make a total of at least 12 different sequences that could be displayed to the subject.

The entire process was repeated for the contralateral eye by patching the right eye. In total, 26 reading charts were shown to the subject. The results were compiled and scored quantitatively for accuracy and reading speed. Scores were provided for each of the different brightness/contrast conditions and the weighted to provide a cumulative score.

All publications cited in this specification as well as U.S. provisional patent application No. 62/077,286, filed Nov. 9, 2014 from which this application claims the benefit of priority, are incorporated herein by reference. While the invention has been described with reference to particular embodiments, it will be appreciated that modifications can be made without departing from the spirit of the invention. Such modifications are intended to fall within the scope of the appended claims.

REFERENCES

1. Radner, "Reading performance of monofocal pseudophakic patients with and without glasses under normal and dim light conditions", J. Cataract Refract. Surg., 40(3): 369-75, March 2014
2. Barot, "Reading performance in infantile nystagmus", Ophthalmology, 20(6):1232-8, June 2013; Epub: Feb. 22, 2013
3. Dexl, "Reading performance and patient satisfaction after corneal inlay implantation for presbyopia correction: two-year follow-up", J. Cataract Refract. Surg. 38(10):1808-16, October 2012; Epub: Aug. 22, 2012
4. Rasp, "Bilateral reading performance of 4 multifocal intraocular lens models and a monofocal intraocular lens under bright lighting conditions", J Cataract Refract Surg. 38(11):1950-61, November 2012
5. Dexl, "Reading performance after implantation of a modified corneal inlay design for the surgical correction of presbyopia: 1-year follow-up", Am. J. Ophthalmol., 153(5):994-1001, May 2012; Epub: Nov. 20, 2011
6. Burggraaff, "Feasibility of the Radner Reading Charts in low-vision patients", Graefes Arch. Clin. Exp. Ophthalmol., 248(11):1631-7, November 2010; Epub: May 25, 2010
7. Gall, "Parafoveal vision impairments and their influence on reading performance and self-evaluated reading abilities", Graefes Arch. Clin. Exp. Ophthalmol. 248(6):863-75, June 2010; Epub: Feb. 16, 2010
8. Finger, "Reading performance is reduced by parafoveal scotomas in patients with macular telangiectasia type 2", Invest. Ophthalmol. Vis. Sci. 50(3):1366-70, March 2009; Epub: Nov. 7, 2008
9. Maaijwee, "Reliability testing of the Dutch version of the Radner Reading Charts", Optom. Vis. Sci., 85(5):353-8, May 2008

10. Alio, "Design of short Spanish sentences for measuring reading performance: Radner-Vissum test", J. Cataract Refract. Surg., 34(4):638-42, April 2008
11. Kiss, "Reading performance of patients with uveitis-associated cystoid macular edema", Am. J. Ophthalmol., 142(4):620-4, October 2006
12. Stifter, "Monocular and binocular reading performance in children with microstrabismic amblyopia", Br J Ophthalmol., 89(10):1324-9, October 2005
13. Richter-Mueksch, "Differences in reading performance of patients with Drusen maculopathy and subretinal fibrosis after CNV", Graefes Arch. Clin. Exp. Ophthalmol., 244(2):154-62, February 2006, Epub: Jul. 27, 2005
14. Stifter, "Evaluating reading acuity and speed in children with microstrabismic amblyopia using a standardized reading chart system", Graefes Arch. Clin. Exp. Ophthalmol., 243(12):1228-35, December 2005, Epub: Jul. 8, 2005
15. Stifter, "Reading performance depending on the type of cataract and its predictability on the visual outcome", J. Cataract Refract. Surg., 30(6):1259-67, June 2004
16. Stifter, "Reliability of a standardized reading chart system: variance component analysis, test-retest and inter-chart reliability", Graefes Arch. Clin. Exp. Ophthalmol., 242(1):31-9, January 2004; Epub: Dec. 10, 2003
17. Colenbrander, "Low vision rehabilitation: visual acuity measurement in the low vision range", J. Ophthalmic Nurs. Technol., 11(2):62-9, March-April 1992
18. Binkhorst, "Determination of the power of a convex-plano intraocular lens in situ from the dioptric keratometer reading of its front surface: extension table for the Javal-Schi-Vntz ophthalmometer", Br. J. Ophthalmol., 71(6):473-6, June 1987

What is claimed is:

1. A method for examining the vision of a subject or monitoring the progression or treatment of an ocular disease in said subject, said method comprising:
displaying a first passage of text at high image contrast from 1.70 to about 2.25 log units, high illumination from about 200 to about 500 cd/m$^2$, or a combination thereof on a screen to a subject having peripheral-to-central vision loss, central-to-peripheral vision loss, cone-rod photoreceptor degeneration, rod-cone photoreceptor degeneration, or rod-cone photoreceptor vision loss; wherein said subject reads said first passage of text;
(ii) displaying a second passage of text at low image contrast from about 0.0 to about 1.35 log units, low illumination from about 1 to about 50 cd/m$^2$, or a combination thereof on said screen; wherein said subject reads said second passage of text; and
(iii) scoring results obtained from steps (i) and (ii),
wherein the subject's head is in a fixed position while reading said first and second passages to evaluate the subject's field of vision.

2. The method according to claim 1, wherein said screen is a computer monitor, TV monitor, snellen chart, projection screen, projection goggles, optical head-mounted display or a high resolution monitor.

3. The method according to claim 1, further comprising applying one or more conditions to the subject selected from:
(a) positioning said subject about 0.5 to about 4 m from said screen;
(b) preventing movement of the subject during the method;
(c) allowing the eyes of said subject to be not dilated;
(d) allowing said subject to wear optical correction; or
(e) covering said subject's contralateral eye.

4. The method according to claim 1, further comprising examining one eye individually or examining both eyes simultaneously.

5. The method according to claim 1, wherein said text is displayed in serif, sans serif, slab serif, semi-serif, monospace, script, blackletter, nonlatin, Unicode, dingbat/symbol, or display/decorative; or said text comprises optotypes or the geometric proportions of said text are constant.

6. The method according to claim 1, wherein said scoring comprises compiling the results of steps (i) and (ii), quantitating the compiled results, and weighting the quantitated results to provide a cumulative score; or wherein step (iii) is based on accuracy and reading speed of said subject.

7. The method according to claim 1, further comprising
displaying to the subject a flash of light at a suitable intensity and for a suitable duration to temporarily bleach the subject's photoreceptors prior to displaying the first passage, and measuring the time required for the photoreceptors to recover so that the subject can read the first passage, and
measuring visual acuity, light sensitivity or contrast sensitivity of said subject.

8. The method according to claim 1, further comprising:
treating said subject for vision loss prior to or after conducting steps (i), (ii) and (iii); or
adjusting said subject's treatment of said disease after conducting steps (i), (ii) and (iii).

9. The method according to claim 8, further comprising displaying to the subject a flash of light at a suitable intensity and for a suitable duration to temporarily bleach the subject's photoreceptors prior to displaying the first passage, and measuring the time required for the photoreceptors to recover so that the subject can read the first passage; and measuring visual acuity, light sensitivity or contrast sensitivity of said subject.

10. The method according to claim 8, wherein said treating comprises gene therapy, cell therapy, pharmaceutical therapy, or device intervention or said device intervention comprises retinal neurostimulus chip implant or a light stimulation unit.

11. The method according to claim 10, wherein said cell therapy comprises transplantation of fetal-derived retinal progenitor cells, induced pluripotent stem cells, embryonic stem cells, retinal pigment epithelium cells, or cells encased in a capsule; or wherein said pharmaceutical therapy comprises administering one or more of acetazolamide, apraclonidine HCl, betaxolol HCl, bimatoprost, brimonidine tartrate, brinzolamide, carbachol, dorzolamide HCl, latanoprost levobunolol HCl, methazolamide, metipranolol, pilocarpine HCl, timolol maleate, timolol hemihydrate, tafluprost, travaprost, prednisolone, moxifloxacin, vitamin A, beta-carotene, docosahexaenoic acid, acetazolamide, corticosteroid, calcium channel blocker, lutein, zeaxanthin, valproic acid, aspirin, anti-inflammatory agents, warfarin, heparin, alteplase, fibrinolytic agent, corticosteroid, alteplase, ranibizumab, aflibercept, triamcinolone, bevacizumab, or dexamethasone; or wherein said device intervention comprises oxygen therapy, surgery, cryotherapy, photocoagulation, diathermy, isovolemic hemodilution, or plasmapheresis; or wherein said gene therapy comprises adeno-associated virus therapy, lentivirus therapy, adenovirus therapy, or non-viral gene delivery.

12. The method of claim 1, wherein the ocular disease is choroideremia.

13. An electronic system for clinical examination of vision system functioning of a subject, said system comprising:
- a first unit configured to display a first passage of text at high image contrast from 1.7 to about 2.25 log units, high illumination from about 200 to about 500 cd/m$^2$, or a combination thereof, and to display a second passage of text at low contrast from about 0.0 to about 1.35 log units and low illumination from about 1 to about 50 cd/m$^2$, or a combination thereof;
- a second unit configured to receive feedback from said subject;
- a first processor configured to receive said feedback;
- a second processor configured to calculate the number of errors in said feedback and provide a score; and
- a means for displaying a flash of light to the subject prior to displaying text and a processor configured to measure recovery time from the occurrence of the flash to the time the subject is able to read the text.

14. The electronic system according to claim 13, further comprising:
- (a) said first unit configured to project instructions to said subject;
- (b) said second unit comprising recordable media or voice recognition software;
- (c) said first unit configured to display text comprising 2 to about 24 passages;
- (d) said first unit configured to display passages of text sequentially;
- (e) said second passage of text comprising 2 to about 24 passages of text;
- (f) a means for instructing said first unit to project said text, wherein said means comprises a mechanical button adjacent to said first unit and connected to said first unit through a first conduit or a computer-generated button; or
- (g) any combination of two or more of (a) through (f).

15. An electronic vision testing device, said device comprising at least one processing unit configured to:
- acquire data using a first passage of text displayed at high image contrast from 1.7 to about 2.25 log units, high illumination from about 200 to about 500 cd/m$^2$, or a combination thereof, on a screen;
- acquire data using a second passage of text displayed at low image contrast from about 0.0 to about 1.35 log units, low illumination from about 1 to about 50 cd/m$^2$ from about 1 to about 50 cd/m$^2$, or a combination thereof on said screen; and
- calculate a score from said data, wherein said score is the percentage of errors in said data;
- wherein said processing unit is configured to acquire data from a bleaching step and correlate the subject's recovery time from the bleaching effect to said score.

16. The electronic vision testing device according to claim 15, comprising:
- (a) a code for displaying a first passage of text at high image contrast from 1.7 to about 2.25 log units, high illumination from about 200 to about 500 cd/m$^2$, or a combination thereof on a screen;
- (b) a code for displaying a second passage of text at low image contrast from about 0.0 to about 1.35 log units, low illumination from about 1 to about 50 cd/m$^2$, or a combination thereof on said screen;
- (c) at least one processing unit for executing said code of (a)-(b);
- (d) at least one processing unit for storing text entered by a subject; and
- (e) calculating the score by comparing the number of errors in said subject's text.

17. The device according to claim 16, further comprising a code and a processing unit for displaying a bleaching flash of light and calculating recovery time from the flash to the scoring of (e).

18. A computer program product, stored on a computer readable medium, said product comprising instructions for configuring a computer to:
- acquire data using a first passage of text displayed at high image contrast from 1.7 to about 2.25 log units, high illumination from about 200 to about 500 cd/m$^2$, or a combination thereof on a screen by a subject reading said first passage of text;
- acquire data using a second passage of text displayed at low image contrast from 0.0 to about 1.35 log units, low illumination from about 1 to about 50 cd/m$^2$ from about 1 to about 50 cd/m$^2$, or a combination thereof on said screen by said subject reading said second passage of text; and
- calculate a score from said data, wherein said score is the percentage of errors in said data; and
- acquire data from a bleaching step and correlate the subject's recovery time from the bleaching effect to said score.

* * * * *